United States Patent
Dunfee et al.

(10) Patent No.: US 7,445,608 B2
(45) Date of Patent: Nov. 4, 2008

(54) AMBULATORY SPINAL UNLOADING METHOD AND APPARATUS

(75) Inventors: Matthew J. Dunfee, Belle Plaine, MN (US); Susan J. Dunfee, Belle Plaine, MN (US)

(73) Assignee: Dunfee & Dunfee LLC, Belle Plaine, MN (US)

( * ) Notice: Subject to any disclaimer, the term of this patent is extended or adjusted under 35 U.S.C. 154(b) by 201 days.

(21) Appl. No.: 11/094,862

(22) Filed: Mar. 31, 2005

(65) Prior Publication Data
US 2006/0149178 A1 Jul. 6, 2006

Related U.S. Application Data

(63) Continuation-in-part of application No. 11/035,485, filed on Nov. 15, 2005, now abandoned.

(60) Provisional application No. 60/640,479, filed on Dec. 30, 2004.

(51) Int. Cl.
*A61F 5/00* (2006.01)
*A61F 5/37* (2006.01)
*A61G 15/00* (2006.01)
*A61B 19/00* (2006.01)

(52) U.S. Cl. .................. 602/19; 602/5; 602/32; 128/845; 128/869; 128/874

(58) Field of Classification Search .......... 602/5, 602/19, 32–35; 128/845–846, 869–87, 874, 128/876
See application file for complete search history.

(56) References Cited

U.S. PATENT DOCUMENTS

| | | | |
|---|---|---|---|
| 3,029,810 A * | 4/1962 | Verner ................. | 602/19 |
| 3,420,230 A | 1/1969 | Ballard | |
| 3,548,817 A * | 12/1970 | Mittasch ................. | 602/36 |
| 5,158,098 A | 10/1992 | Armen | |
| 5,320,641 A | 6/1994 | Riddle et al. | |
| 5,437,617 A | 8/1995 | Heinz et al. | |
| 5,462,518 A * | 10/1995 | Hatley et al. ........... | 602/36 |
| 5,651,764 A * | 7/1997 | Chiu ....................... | 602/36 |
| 5,704,904 A | 1/1998 | Dunfee | |
| 5,724,993 A | 3/1998 | Dunfee | |
| 6,533,740 B2 | 3/1998 | Steven et al. | |
| 5,916,188 A * | 6/1999 | Ousdal ................... | 602/32 |
| 5,950,628 A | 9/1999 | Dunfee | |
| 6,210,354 B1 | 4/2001 | Ousdal | |
| 6,237,602 B1 | 5/2001 | Nickels et al. | |
| 6,689,082 B2 | 2/2004 | Reinecke et al. | |
| 6,702,771 B1 * | 3/2004 | Reinecke et al. ....... | 602/19 |
| 6,749,579 B1 | 6/2004 | Schroder | |
| 6,776,767 B2 | 8/2004 | Reinecke et al. | |
| 6,971,997 B1 | 12/2005 | Ryan et al. | |
| 6,984,217 B2 | 1/2006 | Becerra et al. | |
| 6,997,892 B2 * | 2/2006 | Reinecke ............... | 602/32 |
| 7,070,572 B2 * | 7/2006 | Reinecke et al. ........ | 602/5 |
| 7,074,201 B2 * | 7/2006 | Reinecke et al. ........ | 602/5 |
| 7,201,729 B2 | 4/2007 | Emsky | |
| 2004/0171974 A1 | 9/2004 | Emsky | |

* cited by examiner

*Primary Examiner*—Patricia Bianco
*Assistant Examiner*—Brandon Jackson
(74) *Attorney, Agent, or Firm*—Dardi & Associates, PLLC

(57) ABSTRACT

An ambulatory spinal unloading method and apparatus are implemented to achieve a desired minimum level of residual cushioning in response to a biasing force applied to the associated apparatus tensioning and/or compression mechanism(s). The ambulatory spinal unloading apparatus may further include a treatment system to provide desired levels of nerve and/or muscle stimulation in addition to hot and/or cold elements to provide further therapeutic effects as desired or necessary.

29 Claims, 13 Drawing Sheets

AMBULATORY SPINAL UNLOADING METHOD AND APPARATUS

CLAIM TO PRIORITY OF PROVISIONAL APPLICATION

This application is a Continuation-in-Part of U.S. patent application Ser. No. 11/035,485 (abandoned), filed on Nov. 15, 2005 and further claims priority under 35 U.S.C. § 119 (e)(1) of U.S. Provisional Application Ser. No. 60/640,479 filed on Dec. 30, 2004.

BACKGROUND OF THE INVENTION

1. Field of the Invention

This invention relates generally to methods and apparatus that may employ electrical stimulation and/or hot/cold compresses, among other things, for alleviating pain due to abnormalities associated with, but not limited to, body weight, internal organs, muscles and various spinal infractions, and more particularly, to a method and apparatus for implementing ambulatory spinal unloading.

2. Description of the Prior Art

Traction has long been the treatment of choice for alleviating pain due to certain bodily abnormalities associated with, but not necessarily limited to, internal organs, muscles, body and various spinal infractions. U.S. Pat. No. 6,749,579 B1, entitled *Traction Garment*, issued Jun. 15, 2004 to Schroder, for example, discloses a non-stationary or ambulatory traction garment that includes a plurality of tension spreaders to provide injury-specific traction while restricting unwanted and potentially injurious motions.

Other U.S. patents, e.g. U.S. Pat. No. 5,704,904, issued Jan. 6, 1998 to Dunfee; U.S. Pat. No. 5,724,993, issued Mar. 10, 1998; and U.S. Pat. No. 5,950,628, issued Sep. 14, 1999 to Dunfee, the inventor of the present invention, each disclose use of an ambulatory, wearable support for applying an extending force or traction to a portion of the human anatomy while being worn. These wearable supports employ a plurality of extender sets having at least one selectively inflatable bladder.

U.S. Pat. No. 6,689,082 B2, and U.S. Pat. No. 6,776,767 B2, issued Feb. 10, 2004 and Aug. 17, 2004 respectively to Reinecke et al., disclose an ambulatory traction device that employs one or more lifting mechanisms configured to apply a decompressive force to a portion of a user's body when positioned around the user's body.

A flexible fluidic force generator capable of applying both an extending (traction) force and a compressive force to a portion of the human anatomy while being worn is disclosed in U.S. Pat. No. 6,237,602 B1, entitled *Flexible Fluidic Force Generator*, issued May 29, 2001, to Nickels et al.

While all of the devices described herein above have provided some advances in the field of ambulatory traction devices, they remain deficient in providing an effective residual spinal cushioning or spinal unloading condition, in the absence of a biased tensioning and/or compressive force.

In view of the foregoing, it would be desirable and advantageous in the art to provide a method and apparatus for implementing ambulatory spinal unloading, even in the absence of a biased tensile or traction force to those areas to relieve a portion of the compressive load on the spine to alleviate pain, and to optionally allow proper healing of bodily injuries. It would be further advantageous if the method and apparatus could employ embedded electrodes to deliver electrical stimulation in like fashion to known transcutaneous electrical nerve stimulation (TENS) that are readily available in the market place.

SUMMARY OF THE INVENTION

The present invention is directed to an ambulatory spinal unloading method and apparatus that are implemented by defining a set of desired human characteristics and/or parameters and then implementing an ambulatory traction and cushioning apparatus structure based on the set of human characteristics/parameters to achieve a desired minimum level of residual cushioning, upon deactivating the bias applied to the associated apparatus tensioning and/or compression mechanism(s). The method and apparatus eliminate the absolute necessity for trial and error testing by an end user, and further allow the ambulatory spinal unloading apparatus to be optimized to the desired human characteristic(s) and/or parameter(s). A substantial benefit provided by this optimized apparatus is the avoidance of further inadvertent injuries experienced by an end user due to undesirable trial and error techniques such as those generally associated with apparatus that are already known in the related art. Further, the optimized apparatus will allow an end user in many instances, to wear the apparatus for much longer periods of time than that achievable using known apparatus, without experiencing fatigue. This feature is particularly desirable since it will decrease the level of discomfort generally associated with bodily injuries and thereby benefit a user who is wearing the optimized spinal unloading apparatus. This method and apparatus therefore importantly allows a doctor to prescribe both a tension time period and a compression (non-biased) time period, to yield long term spinal relief. A period of therapeutic electrical stimulation and/or hot/cold pack treatment is desirably prescribed concurrent with for subsequent to the foregoing tension and compression time periods. The desired human characteristics and/or parameters may include, but are not limited to, height, weight, percent of body fat, a plurality of desired circumferential measurements, relative location of human anomaly(s), period of time in traction, amount or percent of body weight, desired traction level(s), length of time and percent of body weight to be subjected to spinal cushioning apparatus, a desired therapeutic application and so on.

In one aspect of the invention, an ambulatory spinal unloading apparatus absorbs undesirable pressure caused by degenerative disc or nerve faucets, using both compression and expansion features provided via a lifter assembly or mechanism.

In another aspect of the invention, an ambulatory spinal unloading apparatus eliminates the necessity to develop time tables and data necessary to formulate correct orthotic belts.

In yet another aspect of the invention, an ambulatory spinal unloading apparatus provides flexible stabilizing effects to yield a desired level of user comfort, even in the absence of activation or biasing of any lifter mechanism(s).

One embodiment of the invention provides a spinal unloading apparatus having an upper or thoracic belt and a lower or lumbar belt in which the thoracic belt and the lumbar belt are separated via a single posterior lifting mechanism. The single posterior lifting mechanism can be formulated, for example, via a single fluidic i.e. piston driven pneumatic chamber in combination with a residual cushioning mechanism such as one or more gel-filled chambers to provide a desired level of residual cushioning upon the removal of fluidic pressure from the fluidic chamber. The single posterior lifting mechanism may optionally be formulated via a mechanically actuated or electro-mechanically actuated device. The mechanically actuated device can be implemented, for example, via a spring structure that may be compressed and released via one or more cam mechanisms. The electro-mechanically actuated device can be implemented, for example, via one or more stepper motors configured to selectively adjust one or more extension means, i.e. rods. The electro-mechanically actuated device could optionally be implemented, for example, via one or more motor actuated worm gears, belts, or pulley mechanisms, turning one or more threaded extension rods. Regardless, the electro-mechanically actuated device(s) are energy efficient such that the desired lifting effect(s) can be achieved using a portable battery pack that may be rechargeable or a portable power pack that may, for example, receive its primary source of power from an automotive accessory outlet. The thoracic belt and the lumbar belt are sufficiently rigid such that a desired spinal lifting effect can be achieved from the single posterior lifting mechanism. Further, the thoracic belt and the lumbar belt may each comprise one or more internal fluidic chambers strategically located to provide a desired level of user comfort and to prevent restrictive binding of the user's thoracic region. These internal fluidic chambers can be replaced instead by one or more pockets configured to receive hot and/or cold compresses. Additional lifting and/or residual cushioning mechanisms can optionally be positioned between the thoracic and lumbar belts at desired locations to provide a desired lifting and/or residual cushioning effect to the user's anterior region subsequent to attaching the spinal unloading apparatus. These additional lifting and/or residual cushioning mechanisms most preferably are implemented via non-fluidic means whenever the posterior lifting mechanism employs fluidic means, and implemented via fluidic means whenever the posterior lifting mechanism employs non-fluidic means, such that the spinal unloading apparatus never employs more than a single fluidic lifting mechanism.

The orthotic belts comprising the spinal unloading apparatus can optionally be implemented with integral electrodes that are positioned such that a desired level of muscular and/or nerve stimulation can be achieved while a user is wearing the spinal unloading apparatus. Most preferably, these integral electrodes are activated/energized via the portable battery pack or power pack that also provides power to the electro-mechanical lifting mechanism(s). Such muscle and/or nerve stimulation can accelerate the spinal healing process due to a reduction in the level of discomfort/pain associated with spinal unloading that may be experienced by the end user.

The upper, or thoracic, belt, which may have the shape of a vest or shirt, may further have shoulder straps configured to ease user fitting and removal.

BRIEF DESCRIPTION OF THE DRAWINGS

Other aspects, features and advantages of the present invention will be readily appreciated as the invention becomes better understood by reference to the following detailed description when considered in connection with the accompanying drawing figures wherein:

FIG. 7b is a front view illustrating the combination lumbar support and hot/cold element having embedded foam pads shown in FIG. 7a;

Figure 1:
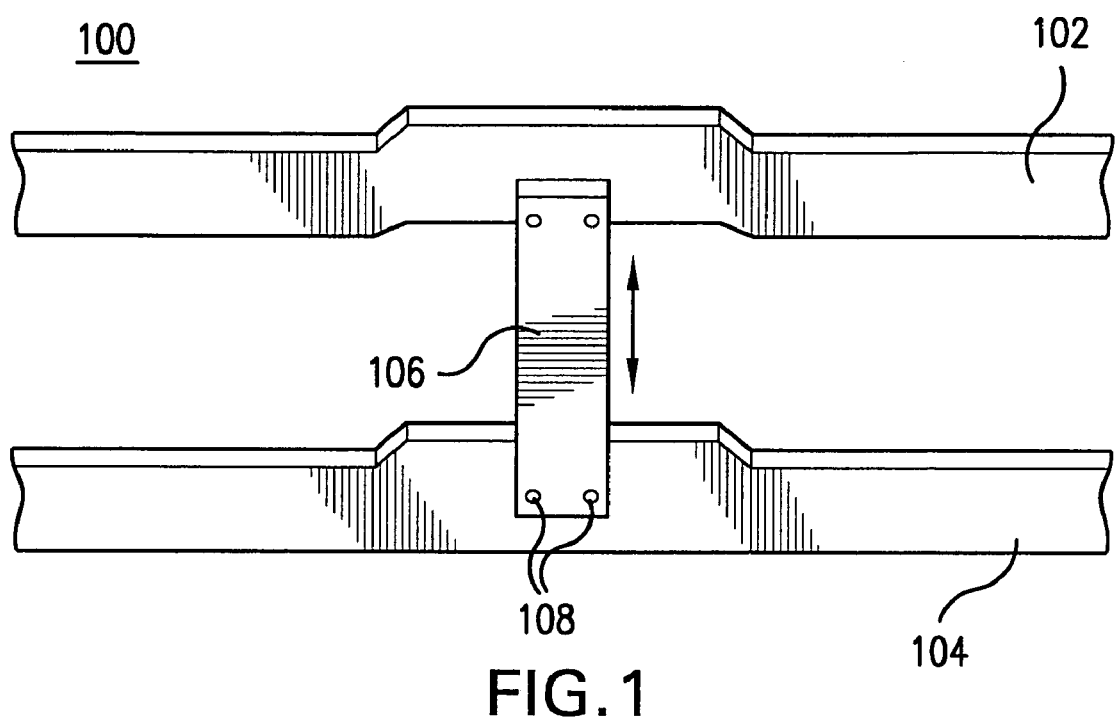
FIG. 1 illustrates a spinal unloading apparatus having a substantially rigid upper thoracic belt, a substantially rigid lower lumbar belt and a single posterior lifting mechanism.

While the above-identified drawing figures set forth particular embodiments, other embodiments of the present invention are also contemplated, as noted in the discussion. In all cases, this disclosure presents illustrated embodiments of the present invention by way of representation and not limitation. Numerous other modifications and embodiments can be devised by those skilled in the art which fall within the scope and spirit of the principles of this invention.

DETAILED DESCRIPTION OF THE PREFERRED EMBODIMENTS

An ambulatory spinal unloading method and apparatus are implemented, as stated herein before, by defining a set of desired human characteristics and/or parameters and then implementing an ambulatory traction and cushioning apparatus structure based on the set of human characteristics/parameters to achieve a desire minimum level of residual cushioning, upon deactivating the associated apparatus biasing mechanism(s). These desired human characteristics/parameters may include, but are not limited to, height, weight, percent of body fat, a plurality of desired circumferential measurements, relative location of human anomaly/anomalies, period of time in traction, amount or percent of body weight to be subjected to spinal cushioning apparatus, desired traction levels, and so on. The ambulatory spinal unloading apparatus is configured to absorb an intermittent and/or unexpected shock and/or vibration using compression and expansion features provided via a lifter assembly such as described herein below with reference to FIGS. 1-12. The ambulatory spinal unloading apparatus may optionally employ electrical nerve and/or muscle stimulation through desired electrodes and may further employ hot and/or cold compresses.

Looking first at FIG. 1, a simple ambulatory spinal unloading apparatus 100 can be seen to include two orthotic belts 102, 104 joined via a single posterior lifter assembly 106 formulated as described in further detail herein below. Lifter assembly 106 can be seen attached to belts 102, 104 via a plurality of attachment elements 108, i.e. rivets. The present invention is not so limited however, and it shall be understood that a plurality of posterior and/or anterior lifter mechanisms/assemblies 106 could just as easily be implemented to provide the desired compression and expansion features and to sustain traction in accordance with the principles of the present invention.

Advantages and features of the present invention will become more readily apparent in view of the known art that generally employs a plurality of lifters/lifter assemblies which result in undesirable rigid traction in the absence of lifter mechanism biasing/activation. With continued reference now to FIG. 1, the upper (thoracic) belt 102 is positioned about a user's thoracic region; while the lower (lumbar) belt 104 is positioned below a user's thoracic region, and is most preferably tightened securely to provide a substantially fixed operating point for the apparatus 100. When the lift mechanism 106 is activated or biased, the apparatus 100 will provide a traction effect. When the lift mechanism 106 is deactivated or unbiased, the apparatus 100 will provide the desired compression and expansion features via the residual cushioning apparatus 110 discussed in further detail herein below. The single posterior lift mechanism 106 can be implemented via a fluidic chamber, such as, for example, an air chamber configured to actuate a piston rod formulated to selectively control separation or distance between the upper and lower belts 102, 104. Lift mechanism 106 can optionally be implemented via a simple pneumatic chamber without the use of a piston rod, such that greater lifting if achieved with greater air pressure, and such that lifting is reduced with decreasing air pressure. Such fluidic devices are well known in the art and so will not be discussed in further detail herein. The present invention is not so limited however; and while known fluidic devices are devoid of residual cushioning effects when the fluidic device is not pressurized, such is not the case in the absence of pressure (bias) when using the fluidic device(s) in accordance with the principles described herein.

Figure 2A:
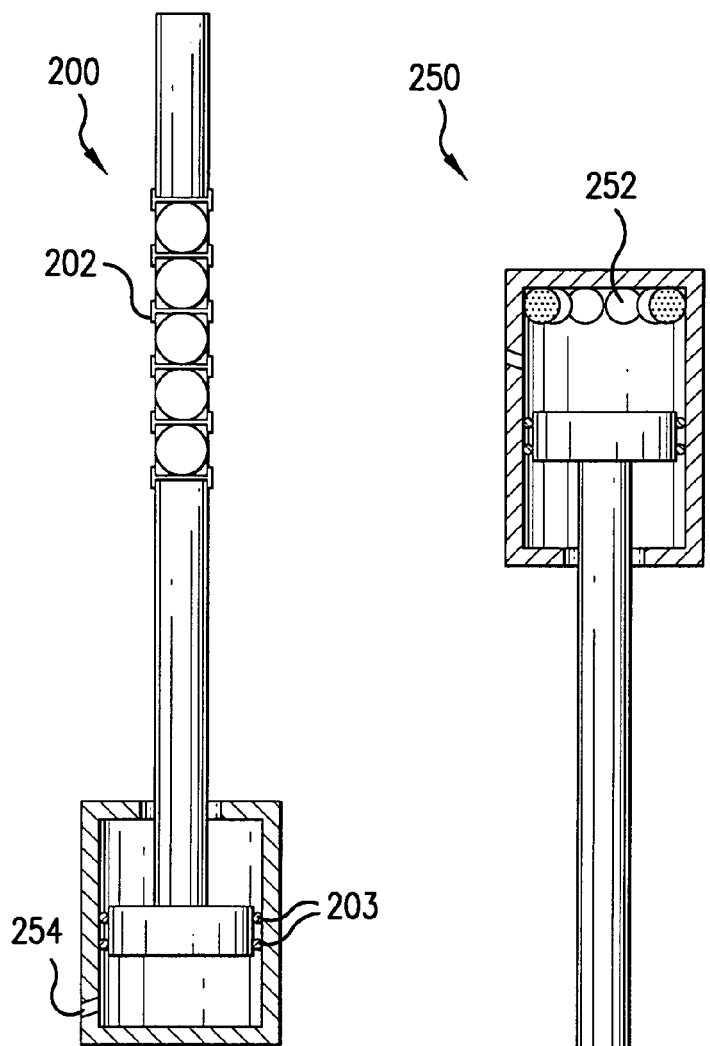
FIG. 2a illustrates a piston actuated fluidic lifting device that employs a residual cushioning spring in accordance with one embodiment of the present invention.

FIG. 2a, for example, illustrates a piston actuated fluidic lifting device 200 that employs a residual cushioning spring 202 and that is suitable for use as the posterior lifting mechanism 106 shown in FIG. 1. Cushioning spring 202 serves to provide a desired level of residual cushioning for an end user in the event fluidic pressure is partially or completely removed from the fluidic chamber. Fluidic lifting device 200 can be seen to employ a fluidic, i.e. air, chamber having a fluidic input port 254 into which a fluidic, i.e. air pressure can be directed. The fluidic pressure serves to move a piston that is sealed via one or more o-ring seals 203.

Figure 2B:
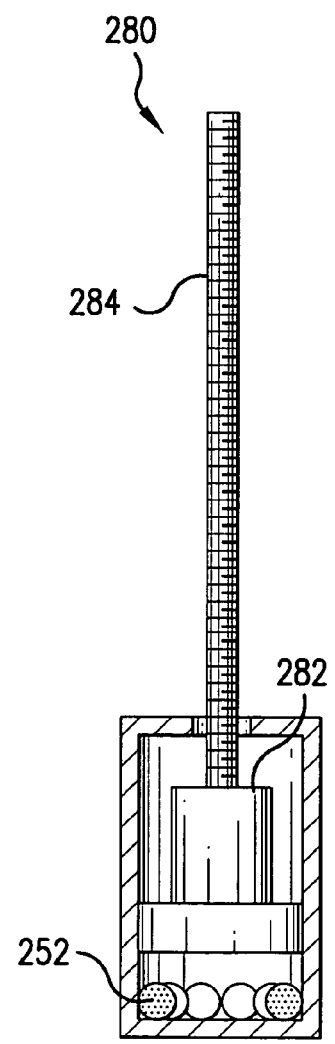
FIG. 2b illustrates a piston actuated fluidic lifting device that employs gel-filled cushion chambers in accordance with one embodiment of the present invention.

FIG. 2b illustrates a piston actuated fluidic lifting device 250 that employs gel-filled cushion chambers 252 and that is also suitable for use as the posterior lifting mechanism 106 shown in FIG. 1. These chambers 252 are compressed when the fluidic lifting device 250 is pressurized via fluidic port 254, to provide the maximum lifting effect. When the fluidic lifting device 250 is depressurized, the gel-filled chamber(s) 252 expand to provide a desired residual cushioning effect. The amount and type of gel that is employed to fill the chamber(s) 252 is selected using well-known engineering principles to provide the desired cushioning effect(s). A percent of a person's body weight may be used by a physician, for example, to determine a criteria associated with desired resistive characteristics to establish the amount and type of gel.

Figure 2C:
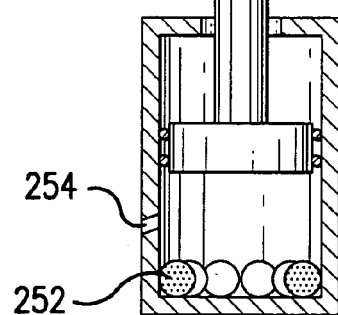
FIG. 2c illustrates device 280 that employs an electric motor driving a worm gear turning a threaded rod in accordance with one embodiment of the present invention.

FIG. 2c illustrates device 280 that employs an electric worm gear motor 282 driving a worm gear turning a screw threaded rod 284, and that is also suitable for use as the posterior lifting mechanism shown in FIG. 1. Residual cushioning in this instance is provided solely via a single lower gel-filled chamber. The gel compresses as the rod 284 is extended, and expands as the rod 284 retracts.

The embodiments described herein with reference to the figures were found by the present inventors to eliminate the necessity to develop time tables and data necessary to formulate acceptable known orthotic belts. Modern ambulatory traction apparatus and devices, for example, are most often designed and manufactured using rigid and narrow semicircular belts which results in too much pressure on any one point of a person's body, and also do not allow enough material area to dissipate large amounts of a person's body weight.

It is noteworthy that, unlike known ambulatory spinal traction/support devices, structures implemented in accordance with the principles described herein make use of mathematical computations associated with human characteristics and/or parameters that may include, for example, but are not limited to, percent of body fat to determine structural related data such as strength, size and length of lift required. This technique then allows for a "one size fits all" lifter structure that may, for example, utilize a single pneumatic biasing mechanism.

Unlike common modern ambulatory traction devices that use various rigid lifter(s) such as assemblies that employ pneumatic pistons, which when unbiased, maintain a rigid device around a person's thoracic region which makes the device difficult to wear when not biased, the embodiments described herein deliver a desired residual amount of cushioning, as stated herein before, upon deactivation of the lifter(s)/lifter assemblies. Values associated with percent of residual cushioning will, of course, depend upon the specific abnormality, but, as discovered by the present inventors, could be as low as about 5 percent of a person's body weight.

Upper and lower orthotic belts 102, 104, as stated herein before, can optionally be formulated to selectively integrate fluidic chambers such as air pockets that function to eliminate restrictive binding of a user's thoracic region when the assembly 100 is worn by the user. These air pockets could instead be replaced with pockets configured to selectively receive hot and/or cold packs. Orthotic belts 102, 104, further may be formulated with a desired quantity of accessory pockets configured to accept inflatable cushions or gel-filled packs that may optionally be temperature controlled to provide a residual cushioning effect in combination with a cold or hot compress effect upon insertion of the gel-filled pack(s) into one or more pockets.

Figure 3:
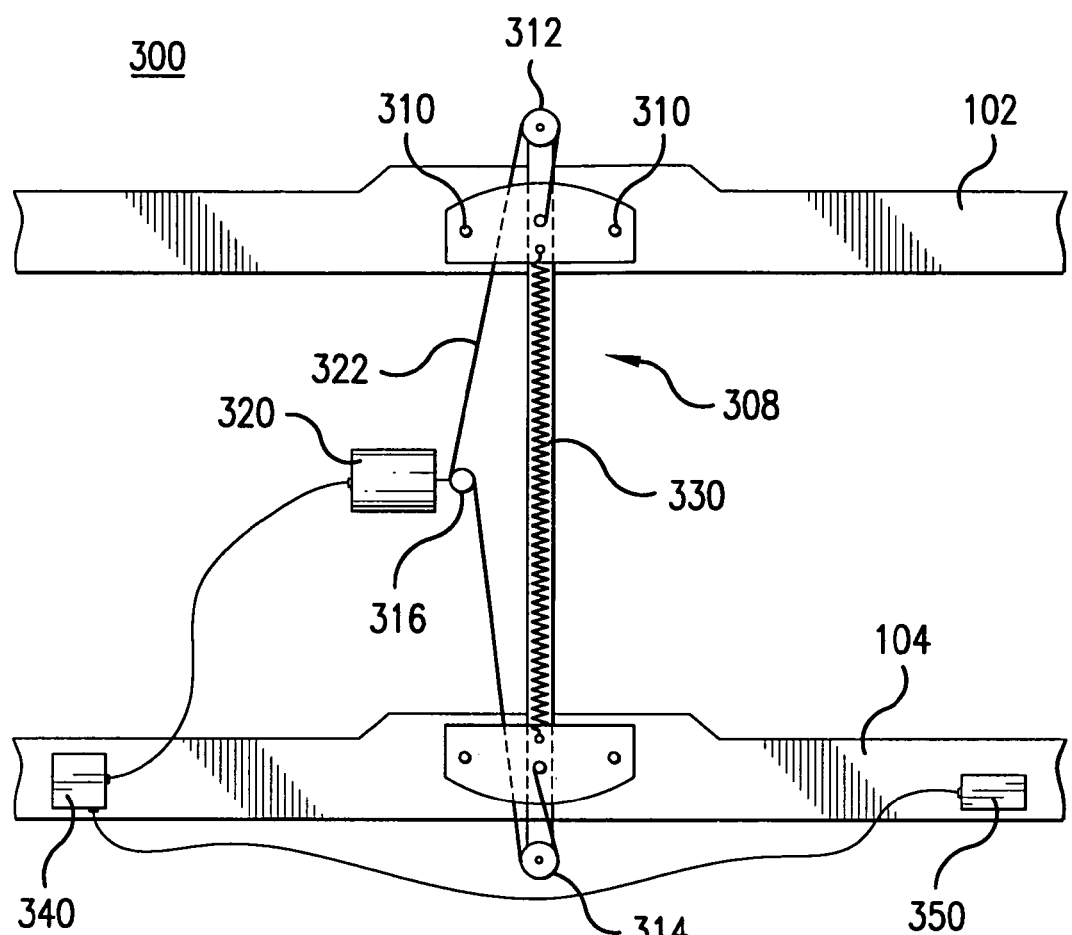
FIG. 3 illustrates another ambulatory spinal unloading apparatus comprising an upper orthotic belt and a lower orthotic belt joined via a single cable/slide assembly posterior lifter mechanism.

FIG. 3 illustrates another ambulatory spinal unloading apparatus 300 comprising an upper thoracic belt 102 and a lower lumbar belt 104 joined via a single posterior lifter mechanism. The Lifter mechanism most preferably can be a single fluidic device that provides the user with a flexible fluidic force capable of applying both an extending (traction)

force and a compressive force to a portion of the human anatomy while being worn. Alternatively, the lifter mechanism can be non-fluidic such that any traction and/or compressive force can be implemented without use of any fluidic pressure. The lifter mechanism, could for example, be implemented via one or more mechanical devices or electro-mechanical devices such as those discussed in further detail herein below. Importantly, ambulatory spinal unloading apparatus 300 comprises no more than a single fluidic lifter mechanism and operates differently than known ambulatory traction and orthotic structures, such that, when used in association with an upper thoracic belt 102, provides a desired amount of residual cushioning or spinal unloading, even when the lifter mechanism is unbiased or inactivated.

With continued reference now to FIG. 3, a lifter mechanism can be seen to include a slide mechanism 308 attached via a plurality of attachment elements 310 to the upper and lower belts 102, 104. Pulleys 312, 314 are attached to the upper and lower belts 102, 104 respectively. Another pulley mechanism 316 is attached to a drive motor assembly 320 that operates a cable assembly 322 to separate the upper and lower belts 102, 104 via slide mechanism 308 as the cable assembly 322 is retracted via pulleys 312, 314 and pulley mechanism 316. A return spring 330 operates to move the belts 102, 104 closer together via slide mechanism 308 as the cable assembly tension is reduced via drive motor assembly 320. The motor assembly 320 is powered via a portable power pack 340 and can include batteries that may be rechargeable. A control mechanism 350 can be seen attached to the lower belt 104; and most preferably can be used by the end user to activate and deactivate drive motor assembly 320 as desired to provide a desired spinal unloading effect.

The cushioned lifter mechanism(s), assemblies and devices described herein with reference to the figures can employ numerous structural materials, such as, but not limited to, metals, plastics, gels and rubbers, to provide a lifter embodiment having both compressive and expansion characteristics such that the inventive ambulatory spinal unloading method and apparatus will provide a flexible stabilizing effect that yields a desired level of user comfort, even when the cushioned lifter mechanism(s) is not activated or biased. Although particular embodiments are described herein using fluidic devices, mechanical devices, and electro-mechanical devices, the present invention is not so limited, and it shall be understood that the desired residual cushioning could just as easily be implemented using particular materials that are commonly employed by those skilled in the mechanical engineering arts and versed in the structural, shock and vibration arts to implement elastomeric damping structures. Such materials may include, but are not limited to, gels, natural rubbers, synthetic resins such as polyvinyl chlorides, polyurethanes, polyamides, polystyrenes, copolymerized polyvinyl chlorides, polyolefin synthetic rubbers, as well as urethanes, EPDM, styrene-butadiene rubbers, nitrites, isoprene, chloroprenes, polypropylene, and silicones.

Figure 4A:
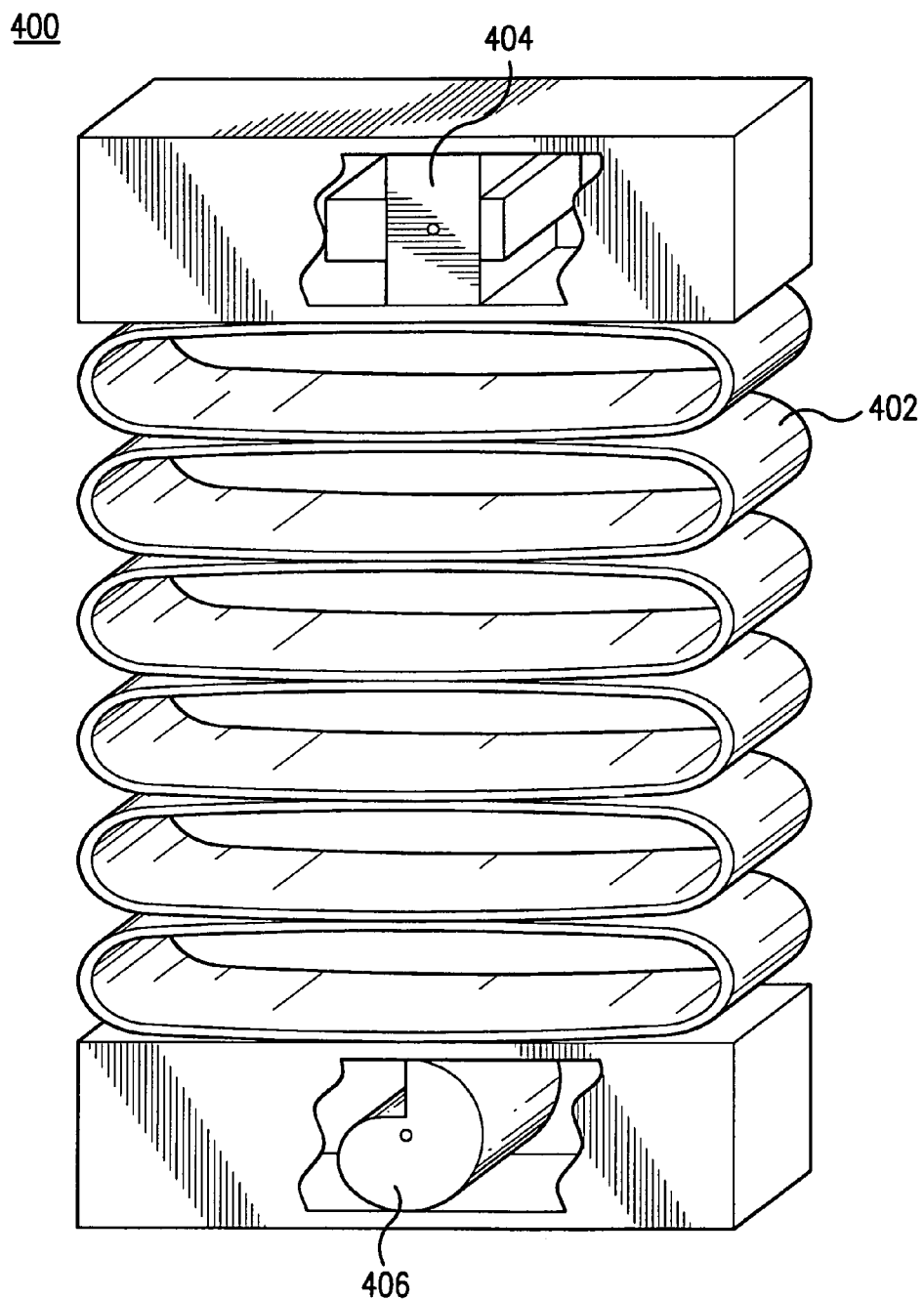
FIG. 4a illustrates a mechanical lifter mechanism that employs a stabilizer spring and a set of mechanical adjusters suitable to form the lifting portion of an ambulatory spinal unloading apparatus such as that shown, for example, in FIG. 1.

FIG. 4a illustrates a mechanical lifter mechanism 400 that employs a stabilizer spring 402 and a set of mechanical adjusters 404, 406 suitable to form the lifting portion of an ambulatory spinal unloading apparatus such as that shown, for example, in FIG. 1. Rotation of either/or mechanical adjuster 404 and mechanical adjustor 406 serves to selectively compress and/or decompress stabilizer spring 402, such that even when the mechanical adjusters 404, 406 are rotated to remove all compressive effects, the stabilizer spring 402 will provide a residual cushioning effect. The amount of residual cushioning effect will vary with the rotation of the mechanical adjusters 404, 406.

Figure 4B:
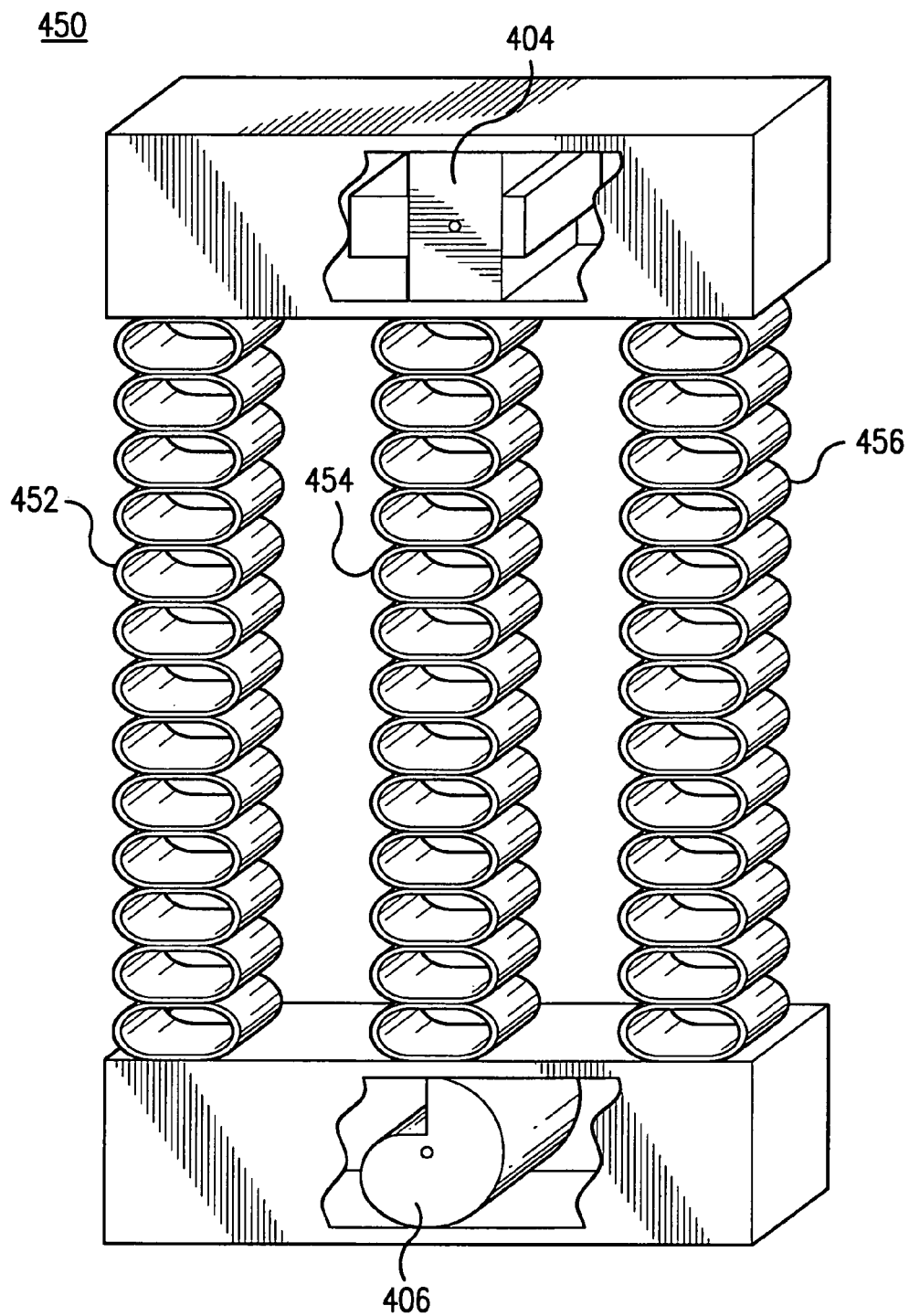
FIG. 4b illustrates another mechanical lifter mechanism that employs a set of stabilizer springs and a set of mechanical adjusters suitable to form the lifting portion of an ambulatory spinal unloading apparatus such as that shown, for example, in FIG. 1.

FIG. 4b illustrates another mechanical lifter mechanism 450 that employs a set of stabilizer springs 452, 454, 456 and a set of mechanical adjusters 404, 406 suitable to form the lifting portion of an ambulatory spinal unloading apparatus such as that shown, for example, in FIG. 1. Biasing of the lifter mechanism(s) 400, 450 is implemented via rotation of one or more of the mechanical adjusters 404, 406. Proper design of the mechanical adjusters 404, 406 will allow for either a biased or unbiased condition. When unbiased, only the stabilizer spring(s) 402, 452, 454, 456 solely will provide the desired residual cushioning effect. The stabilizer springs 402, 452, 454, 456 can be a more conventional steel spring structure, or may, for example, be formulated using any of the elastomeric damping materials referenced herein before.

Figure 5:
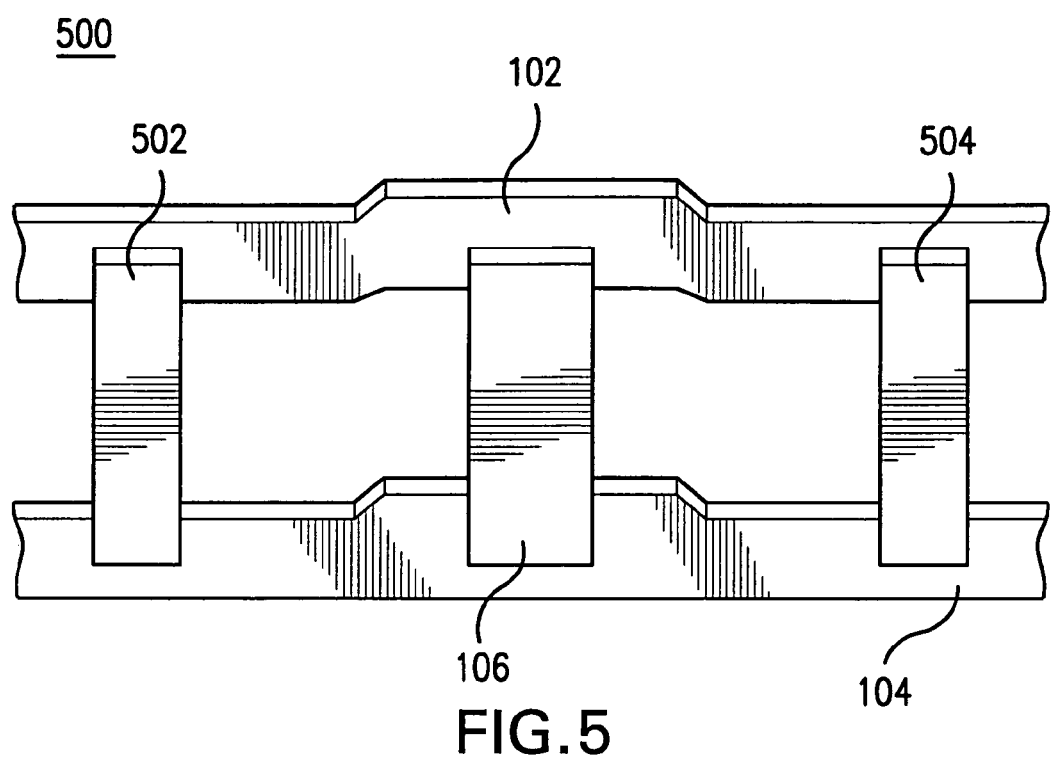
FIG. 5 illustrates an orthotic traction vest comprising an upper belt and a lower belt joined via a single posterior traction lifter and one pair of anterior traction lifters.

Moving now to FIG. 5, an orthotic traction vest 500 is depicted comprising an upper belt 102 and a lower belt 104 joined via a single posterior traction lifter 106 and one pair of anterior traction lifters 502, 504. The single posterior traction lifter 106, as stated herein before, can be any type of biased lifter mechanism, fluidic or non-fluidic, that provides a desired level of user comfort and residual cushioning determined via the human body characteristics and/or parameters as discussed herein before. Lifter mechanism 106, can be, for example, a piston driven air chamber positioned between one or more gel-filled chambers or pockets, such as described herein before. This desired residual cushioning can optionally be implemented via fluidic chambers, e.g. air pockets integrated into one or more of the orthotic belts 102, 104 such that any restrictive binding of a user's thoracic region is also substantially eliminated, even when lifter mechanisms 106, 502, 504 are not activated or biased. The present invention is not so limited, and it shall be understood that lifter mechanisms 106, 502, 504 can be implemented via mechanical and/or electromechanical means so long as the desired residual cushioning and spinal unloading characteristics are achieved according to the principles of the invention discussed herein.

Figure 6:
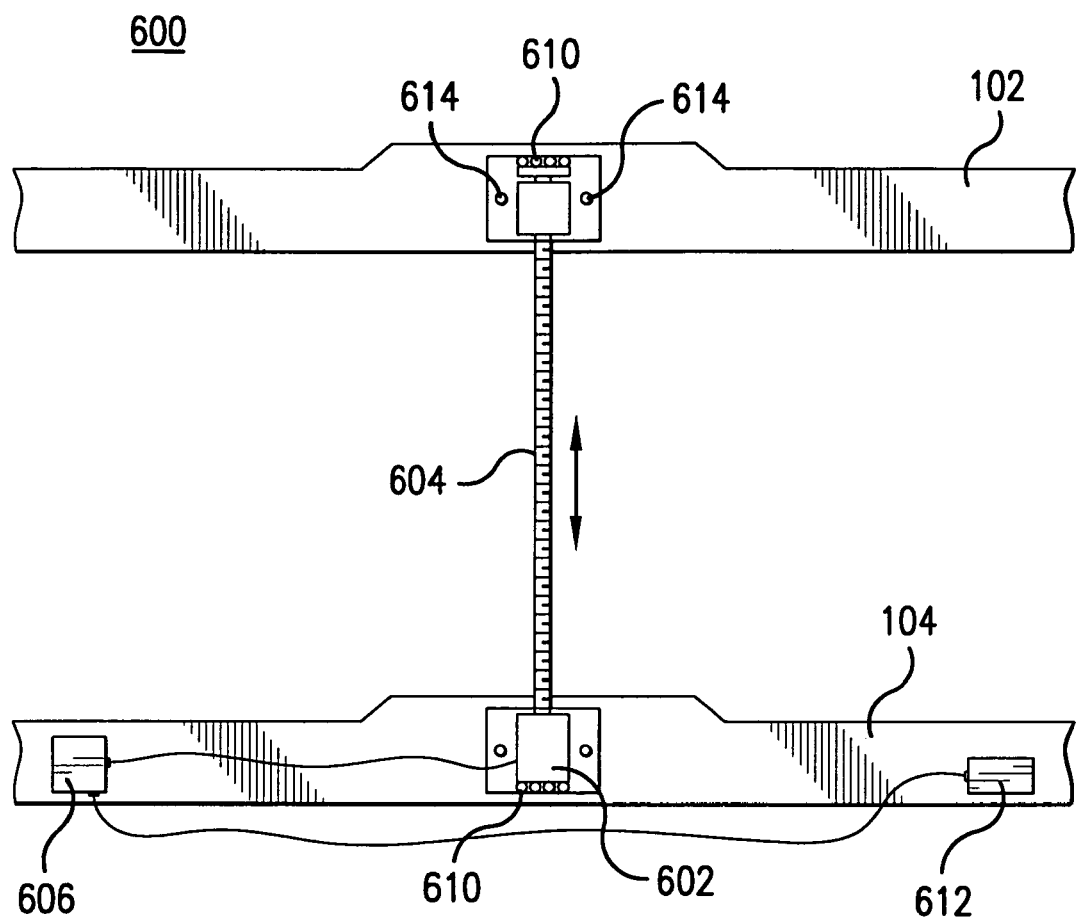
FIG. 6 illustrates an electro-mechanical lifter assembly that is suitable to implement any of the lifter mechanisms depicted in FIGS. 1 and 5.

FIG. 6 illustrates an electro-mechanical lifter assembly 600 that is suitable to implement any of the lifter mechanisms 106, 502, 504. Lifter assembly 600 can be seen to include one or more worm gear drive motors 602 that operate to extend and retract one or more threaded rods 604. The present invention is not so limited however, and it shall be understood that drive motor 602 could just as well be an electric stepper motor that operates to selectively extend or reduce the distance between orthotic belts 102, 104 via a requisite shaft or rod assembly 604. Lifter assembly 600 could further be implemented instead by using belt and pulley techniques discussed herein before, of which numerous suitable motors, pulleys, belts and cables are familiar to those skilled in the art. Power to the electric motor(s) 602 is provided via a portable power or battery pack 606 that may be rechargeable. Since the electro-mechanical lifter assembly 600 presents a rigid lifting effect to the end user, assembly 600 is combined with one or more residual cushioning spring mechanisms 610 such that a desired residual cushioning effect is achieved whenever the motor 602 fully retracts the screw thread or solid rod(s) 604.

Figure 7A:
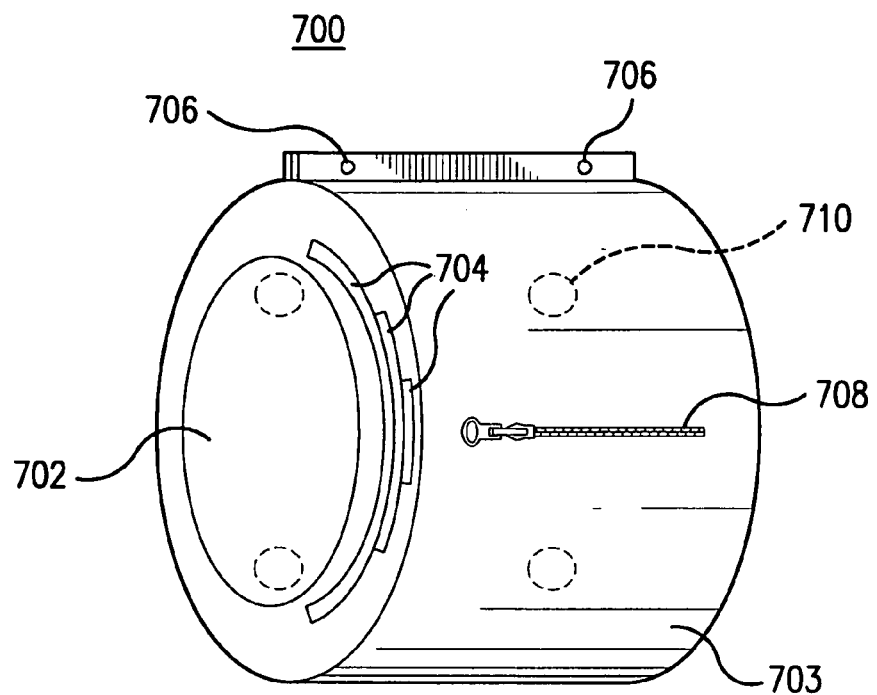
FIG. 7a is a side view illustrating a combination lumbar support and hot/cold element having embedded foam pads.
Figure 7B:
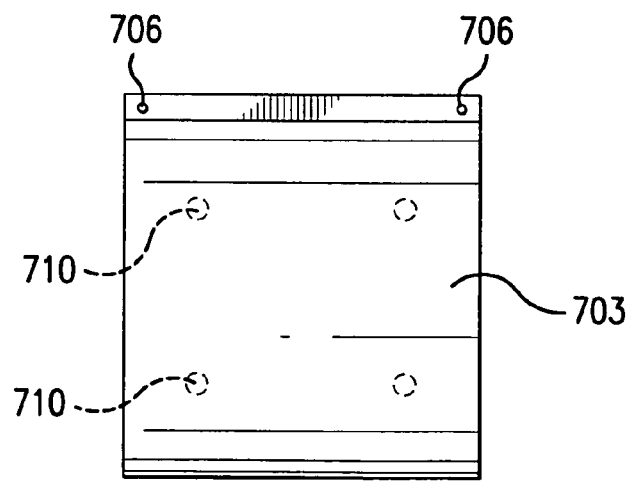

FIGS. 7a and 7b illustrate side and front views respectively for an assembly 700 including a combination lumbar support and hot/cold element 702 having embedded foam pads 704. The assembly 700 exterior is fabricated using a suitable fabric 703 that snaps together at its ends via snap devices 706, and that includes a zippered opening 708 to removably receive one or more foam pads 704 and a desired hot/cold element. Assembly 700 can be seen to be implemented with integrated electrodes 710 strategically placed about the fabric 703 region. These orthotic electrodes 710 may be energized via the electric motor power pack 606 shown in FIG. 6, and are positioned to generate a desired level of muscle and/or nerve stimulation to the user's lumbar region. The benefits and advantages of providing such muscle and/or nerve stimulation are well documented in the art, and so a discussion regarding such benefits and advantages will not be set forth herein in order to provide clarity and to promote brevity. The present inventors, however, are not aware of any structures or applications in which such muscle and/or nerve stimulation electrodes are integrated into the orthotic belt assembly portion or any other portion of an ambulatory traction device or spinal unloading device. In this manner, the orthotic assembly 100, 500 operates to provide spinal unloading and residual cushioning with a substantially reduced level of pain to the end user, in contradistinction to known orthotic assemblies in which the end user often experiences substantial levels of discomfort and pain during activation of the orthotic assembly. In one application, assembly 700 may be inserted into a belt 104 pocket, such as discussed herein before, that is implemented to removably receive such assemblies and/or devices.

Figure 8:
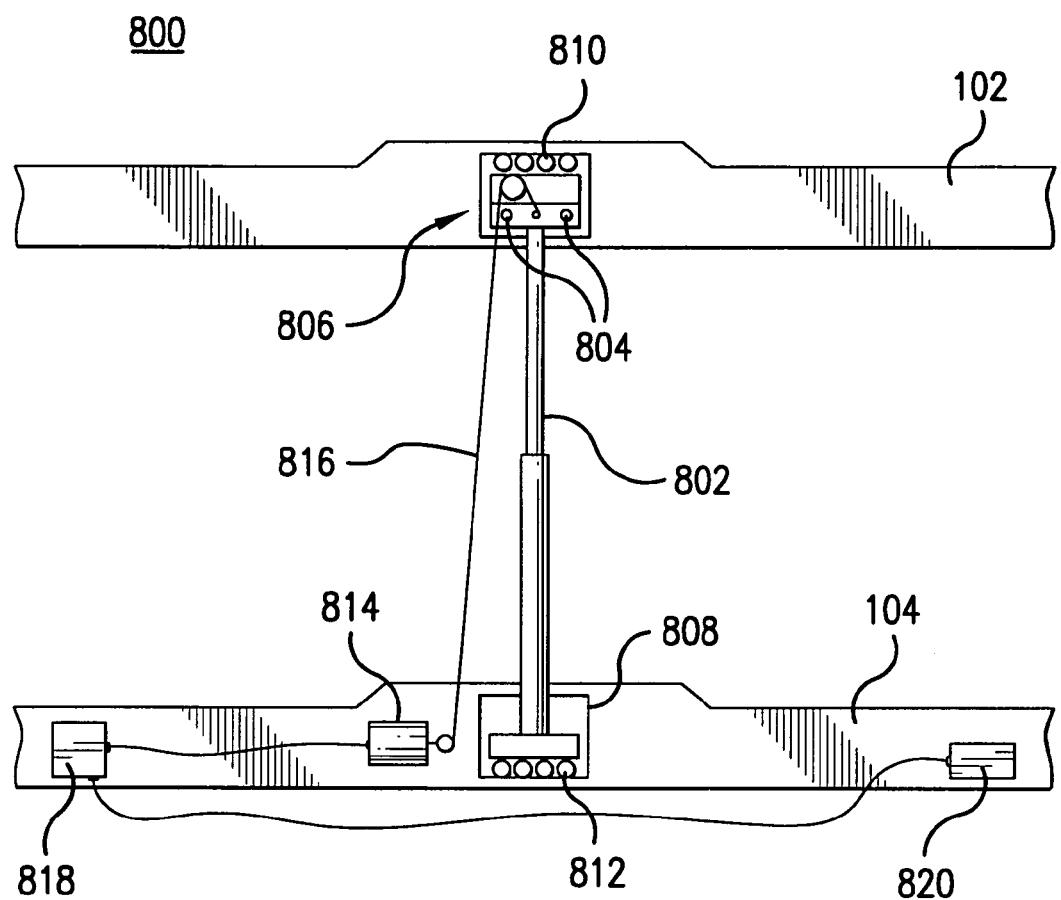
FIG. 8 illustrates an orthotic traction vest comprising an upper belt and a lower belt joined via a single cable/slide type posterior traction lifter mechanism.

FIG. 8 illustrates an orthotic traction vest 800 comprising an upper belt 102 and a lower belt 104 joined via a single cable/slide type posterior traction lifter mechanism 802. Lifter mechanism 802 can be seen to be attached to upper and lower belts 102, 104 via suitable attachment elements 804 such as, but not limited to, rivets and the like. Upper belt 102 can be seen to further include a pulley assembly 806 that operates in response to a cable pulley drive motor 814 to move the cable/slide type lifter mechanism 802. Cable/slide type lifter mechanism 802 can be seen to be anchored within a chamber 808 that comprises a portion of the lower belt 104. Residual spring cushions 810, 812 are strategically placed at each end of the lifter mechanism 802 such that a desired level of residual cushioning is provided whenever the cable/slide assembly is in its minimal belt separation position, i.e. whenever tension is completely released on cable 816 via drive motor 814. Drive motor 814 is powered via a portable power or battery pack 818 that may be rechargeable. A control unit 820 is attached to lower belt 104 that can be user operated to control the amount of separation between upper and lower belts 102, 104 via cable/slide type lifter mechanism 802 in response to drive motor 814.

Figure 9:
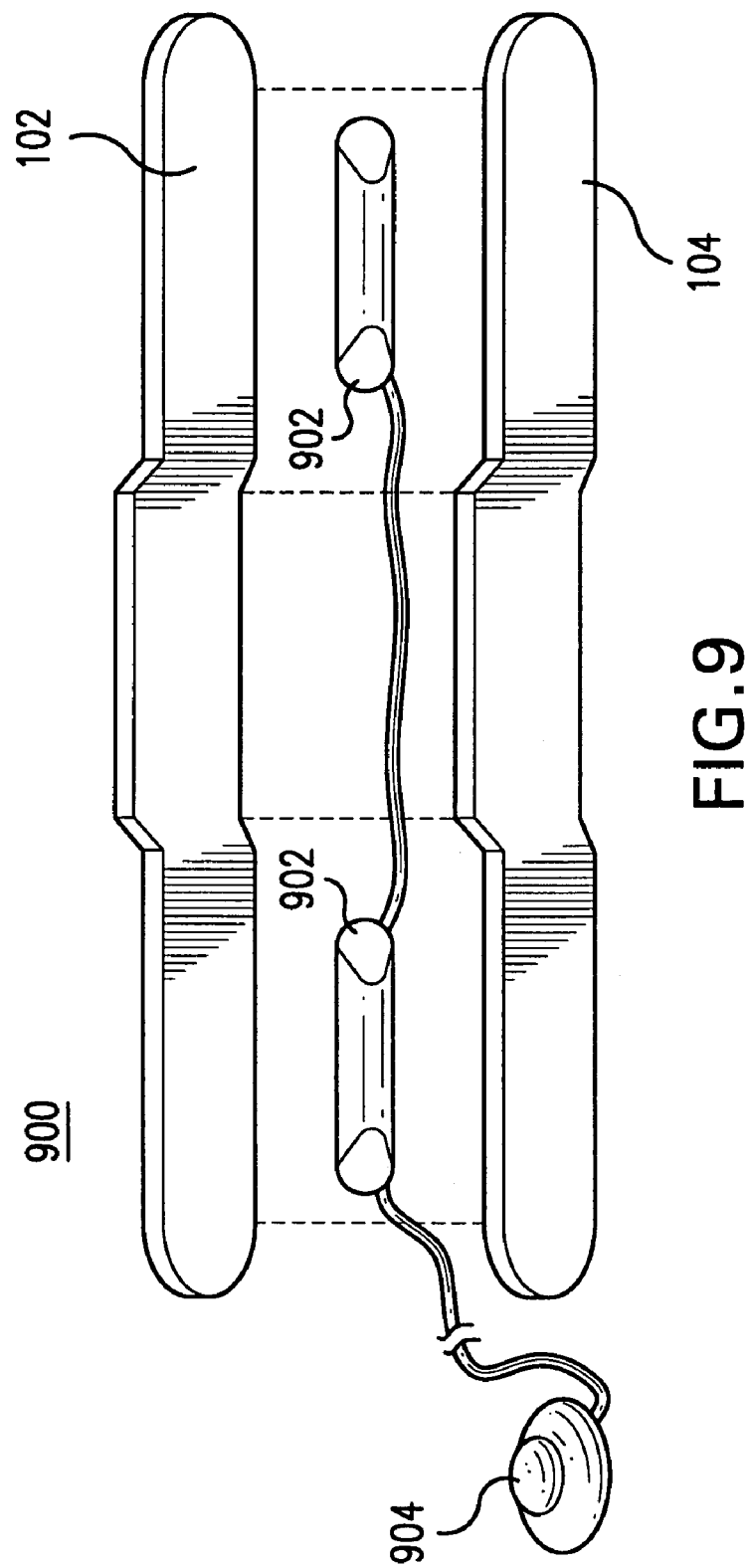
FIG. 9 illustrates a thoracic belt assembly having one or more embedded air bags configured to prevent restrictive binding of a user's thoracic region.

FIG. 9 illustrates a thoracic belt assembly 900 having one or more embedded air bags 902 configured to prevent restrictive binding of a user's thoracic region. An air pump 904 or other suitable fluidic biasing means is provided to supply the requisite fluidic chamber pressure. These air bags 902 could easily be replaced instead with hot/cold compresses, gel-filled packs, cushions, or other types of elements to deliver a desired therapeutic effect to an end user. Thoracic belt 102 could instead employ one or more pockets or opening that are configured to removably receive any of the elements discussed herein above.

Figure 10:
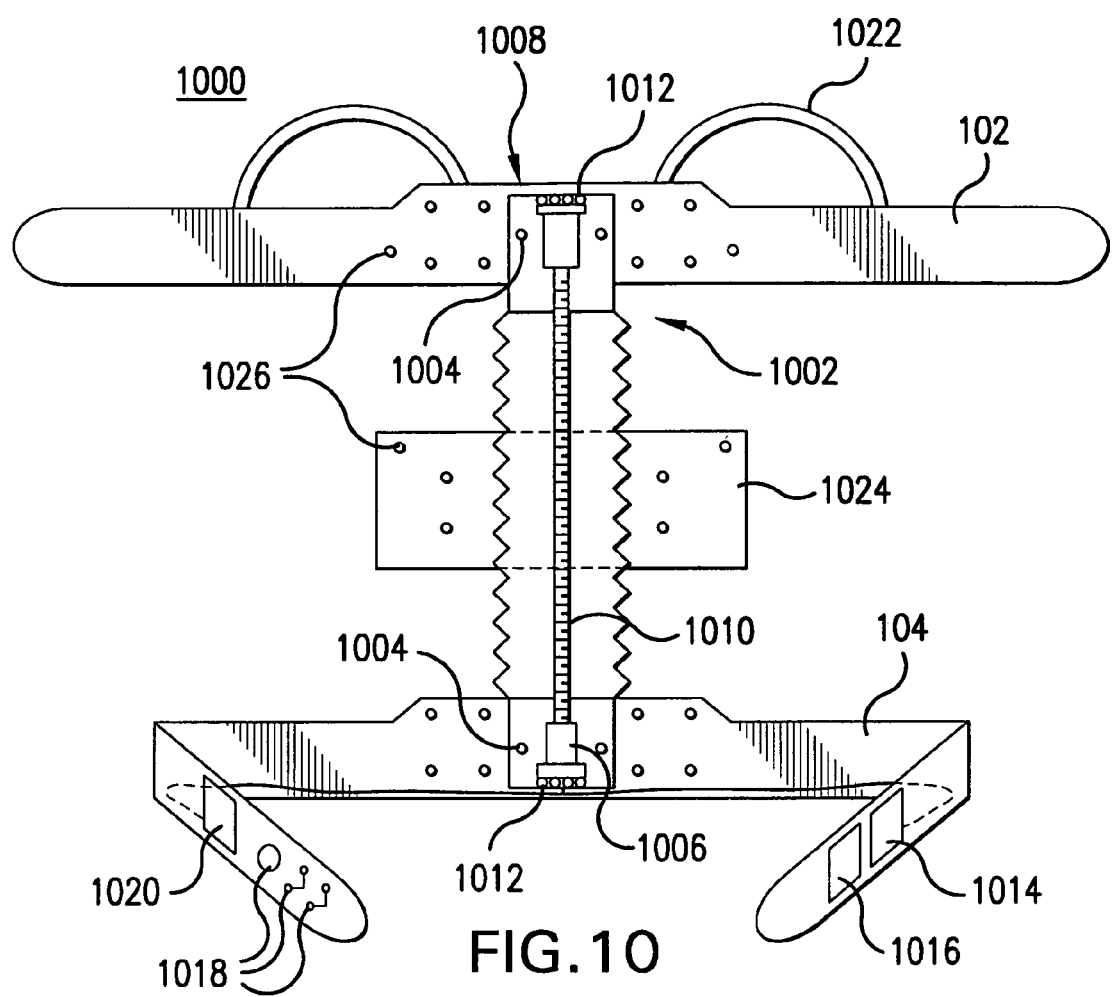
FIG. 10 illustrates a thoracic belt assembly having a plurality of spinal unloading features, therapeutic features and stimulation features according to one embodiment of the present invention.

FIG. 10 illustrates a thoracic belt assembly 1000 having a plurality of spinal unloading features, therapeutic features and stimulation features according to one embodiment of the present invention. Belt assembly 1000 can be seen to include upper (thoracic) belt 102 and lower (lumbar) belt 104. A single posterior lift mechanism 1002 is attached to upper and lower belts 102, 104 via suitable attachment elements 1004. A worm gear drive motor 1006 comprises a lower portion of the lift mechanism 1002; while a threaded screw receiver mechanism 1008 comprises an upper portion of the lift mechanism 1002. A screw rod or threaded rod 1010 is rotated via drive motor 1006 to turn the screw rod 1010 within receiver mechanism 1008 to selectively increase or decrease the distance between upper and lower belts 102, 104. Upper belt 102 can be seen to further include thoracic contact electrodes such as described herein before, and that operate to stimulate certain thoracic nerves and/or muscles as desired. Lower belt 104 can likewise be seen to further include lumbar contact electrodes the operate to stimulate certain lumbar nerves and/or muscles as desired. Residual cushioning springs 1012, such as discussed herein before, are strategically positioned at each end of lift mechanism 1002 to provide a desired level of residual cushioning whenever the lift mechanism 1002 is in its minimal belt separation position. Drive motor 1006 is most preferably powered via an AC and/or DC portable power or battery pack 1014 that may be rechargeable. Control circuitry 1016 is integrated into lower belt 104 and is accessible via user controls 1018 to control separation distance between upper and lower belts 102, 104 as well as strategic nerve and/or muscle stimulation. A recording apparatus 1020, such as, but not limited to, a read/write E-prom, is provided to record strategic traction, spinal unloading, stimulation, and/or therapeutic parameters provided to an end user during the period of time thoracic belt assembly 1000 is worn by the end user. With continued reference now to FIG. 10, upper belt 102 can be seen to also include a pair of shoulder straps 1022 that may be adjustable to comfortably fit the end user and strategically position the thoracic belt assembly 1000 to optimize the desired traction, unloading, stimulation, and/or therapeutic effects. Thoracic belt assembly 1000 can be seen to also include a lumbar pad assembly 1024 having stimulation contact electrodes and other features such as that described herein before with reference to FIGS. 7a and 7b. Snaps 1026 or other suitable means are employed to attach lumbar pad assembly 1024 to the upper belt 104.

Figure 11:
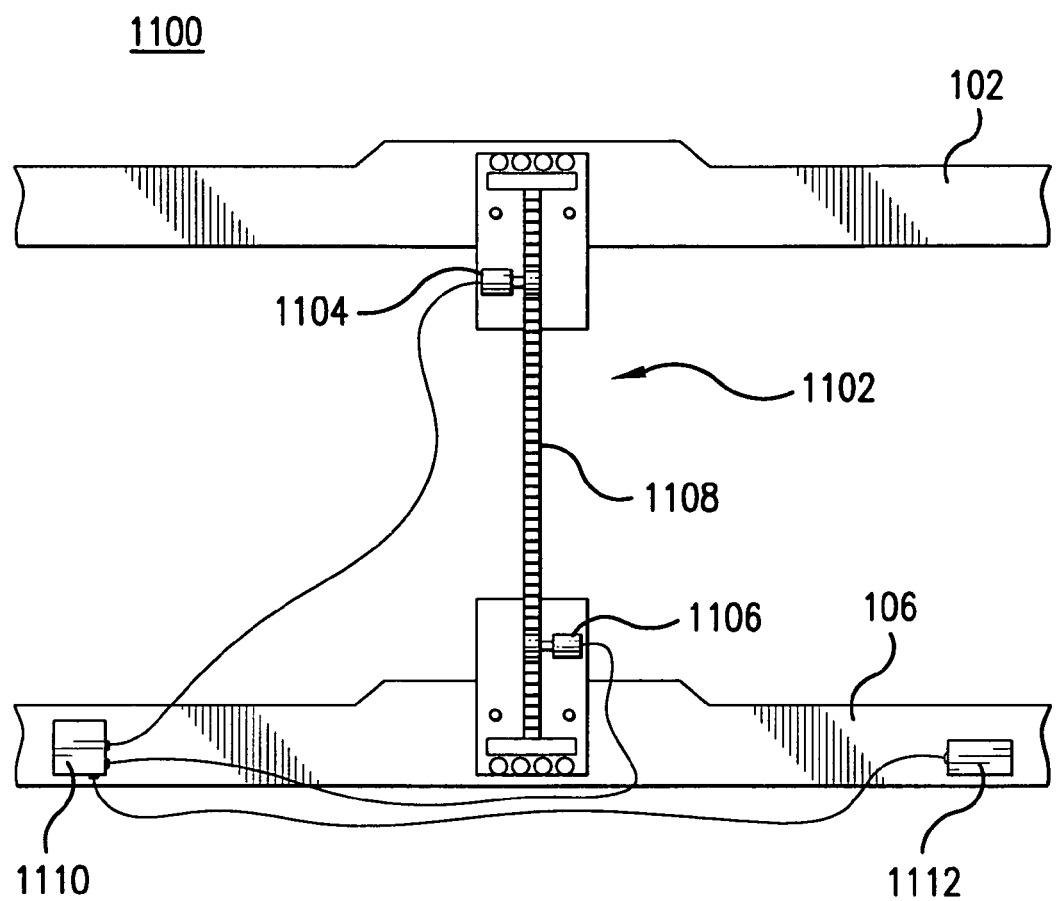
FIG. 11 illustrates an orthotic traction vest comprising an upper belt and a lower belt joined via a single rack and pinion type posterior traction lifter mechanism.

FIG. 11 illustrates an orthotic traction vest 1100 comprising an upper belt 102 and a lower belt 104 joined via a single rack and pinion type posterior traction lifter mechanism 1102. Upper and lower portions of lifter mechanism 1102 are attached to upper and lower belts 102, 104 via suitable attachment elements. The present inventors found rivets to be a suitable attachment element in many applications. Upper portion of lifter mechanism 1102 can be seen to include a first gear drive motor 1104; while lower portion of lifter mechanism 1102 can be seen to include a second gear drive motor 1106. Upper and lower portions of lifter mechanism can be seen to further include springs that operate to provide a residual cushioning effect whenever the lifter mechanism 1002 is in its minimal belt separation position. The present invention is not so limited however, and it shall be understood that this embodiment or any embodiment of the present invention can include any other type of residual cushioning apparatus as discussed or referenced herein before to provide a residual cushioning effect in accordance with the principles set forth herein. Extension rod 1108 has teeth along its entire length that allow each drive motor 1104, 1106 to selectively move the rod 1108 in a desired direction to control the distance between upper and lower belts 102, 104. A portable power/battery pack 1110 is provided to provide power to the drive motors 1104, 1106. Portable power/battery pack 1110 may be an AC and/or DC powered device as desired. An end user operated control circuit 1112 is included to allow an end user to selectively activate each drive motor 1004, 1006 individually or together as desired to achieve a desired spinal unloading effect to the end user.

Figure 12:
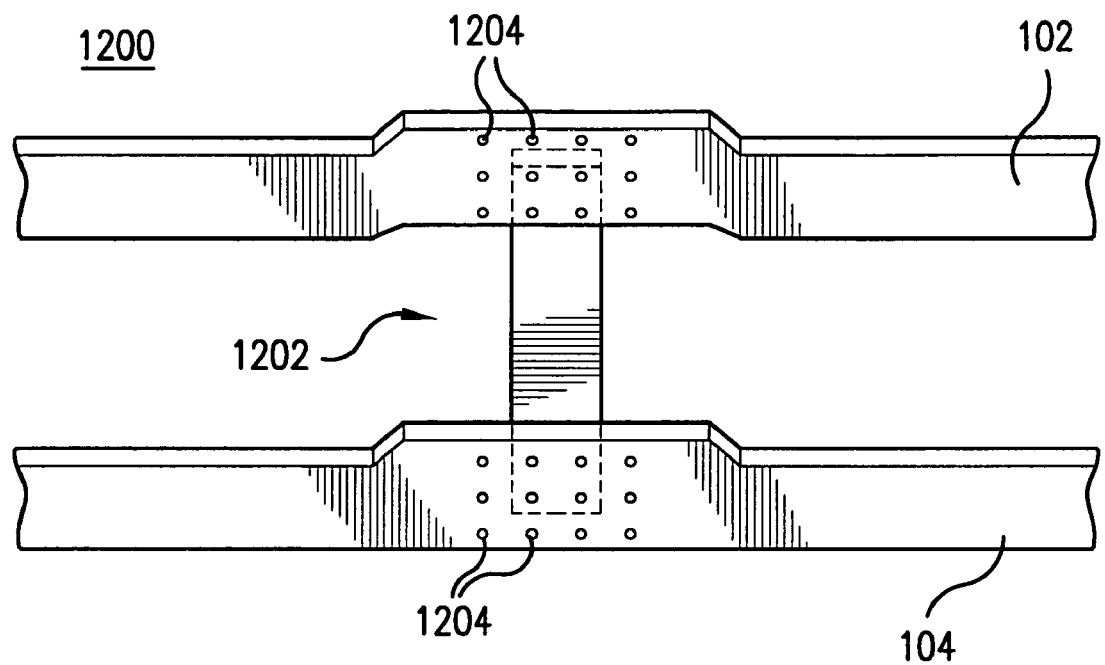
FIG. 12 illustrates an orthotic traction vest comprising an upper belt and a lower belt joined via a single posterior lifter mechanism in which the upper and lower belts comprise electrical stimulation contact electrodes.

FIG. 12 illustrates an orthotic traction vest 1200 comprising an upper belt 102 and a lower belt 104 joined via a single posterior lifter mechanism 1202 in which the upper and lower belts 102, 104 comprise electrical stimulation contact electrodes 1204, such as discussed herein before, to provide a desired level of strategic thoracic and/or lumbar nerve and/or muscle stimulation. Those skilled in the therapeutic arts will readily appreciate that the number and placement of such electrodes will vary and depend upon the therapeutic effect(s) desired from the stimulation when combined with the desired level of spinal unloading provided via orthotic traction vest 1200.

In summary explanation, an ambulatory spinal unloading method and apparatus are implemented by defining a set of desired human characteristics and/or parameters and then implementing an ambulatory traction and cushioning apparatus structure based on the set of human characteristics/parameters to achieve a desired minimum level of residual cushioning, even in the absence of any bias applied to the associated apparatus tensioning and/or compression mechanism(s). This technique eliminates the need for trial and error testing by an end user, and further allows the ambulatory spinal unloading apparatus to be optimized to the desired human characteristic(s) and/or parameter(s). A substantial benefit provided by this optimized apparatus is the avoidance of further inadvertent injuries experienced by an end user due to undesirable trial and error methods associated with apparatus that is already known in the related art. Further, the optimized apparatus will allow an end user in many instances, to wear the apparatus for much longer periods of time than that achievable using known apparatus, without experiencing fatigue. This feature is particularly desirable since it will enhance the healing time associated with bodily injuries that will benefit from wearing the optimized spinal unloading apparatus, especially when the spinal unloading is combined with therapeutic electrical nerve and/or muscle stimulation and/or application of hot and/or cold compresses. The desired human characteristics and/or parameters may include, but are not limited to, height, weight, percent of body fat, a plurality of desired circumferential measurements, relative location of human anomaly(s), period of time in traction, amount or percent of body weight, desired traction level(s), length of time and percent of body weight to be subjected to spinal cushioning apparatus and/or therapeutic treatment, and so on.

In view of the above, it can be seen the present invention presents a significant advancement in the art of spinal unloading and therapeutic treatment. Further, this invention has been described in considerable detail in order to provide those skilled in the engineering and orthotic arts with the information needed to apply the novel principles and to construct and use such specialized components as are required. In view of the foregoing descriptions, it should be apparent that the present invention represents a significant departure from the prior art in construction and operation. However, while particular embodiments of the present invention have been described herein in detail, it is to be understood that various alterations, modifications and substitutions can be made therein without departing in any way from the spirit and scope of the present invention, as defined in the claims which follow. The complete disclosure of all patents, patent documents, and publications are incorporated herein by reference as if individually incorporated.

What is claimed is:

1. An ambulatory spinal unloading apparatus configured to provide a desired amount of traction force to a spine of a patient and to absorb an intermittent and/or unexpected shock and/or vibration, with the traction force provided via a plurality of lifter assemblies, comprising:
   a vest that comprises
      an upper orthotic belt;
      a lower orthotic belt;
      a residual cushioning device; and
      the plurality of lifter assemblies;
   wherein the plurality of lifter assemblies each comprising a worm gear turning a threaded rod or a piston actuated fluidic lifting device that independently expands or retracts to control distance between the orthotic belts to provide the traction force to a spine of a patient, and each of the lifter assemblies further comprises a residual cushioning device wherein the residual cushioning device comprises a spring and/or damper, that independently provides a desired residual cushioning effect by compression of a spring and/or damper to thereby absorb an intermittent and/or unexpected shock and/or vibration, wherein the spring and/or damper is effective to provide the residual cushioning for the rod or for the piston actuated fluidic lifting device in a deactivated state.

2. The spinal unloading apparatus according to claim 1, wherein each of the plurality of lifter assemblies comprises no more than one fluidic chamber.

3. The spinal unloading apparatus according to claim 1, wherein the residual cushioning device comprises a gel-filled chamber.

4. The spinal unloading apparatus according to claim 1, wherein the residual cushioning device comprises the spring.

5. The spinal unloading apparatus according to claim 1, wherein the residual cushioning device comprises the damper.

6. The spinal unloading apparatus according to claim 1, wherein the residual cushioning device comprises the damper.

7. The spinal unloading apparatus according to claim 1, wherein the plurality of lifter assemblies each comprise at least one electric motor configured in combination with a mechanical extension shaft assembly to selectively control the distance between the orthotic belts.

8. The spinal unloading apparatus according to claim 7, further comprising a portable battery pack operational to deliver power to the electric motor.

9. The spinal unloading apparatus according to claim 7, wherein the mechanical extension shaft assembly comprises at least one element selected from the group consisting of belts, pulleys, cables, threaded shafts, and gears.

10. The spinal unloading apparatus according to claim 1, wherein each of die plurality of lifter assemblies comprises at least one stepper motor configured in combination with a mechanical extension shaft assembly to selectively control the distance between the orthotic belts.

11. The spinal unloading apparatus according to claim 10, further comprising a portable battery pack operational to deliver power to the electric motor.

12. The spinal unloading apparatus according to claim 10, wherein the mechanical extension shaft assembly comprises at least one element selected from the group consisting of belts, pulleys, cables, threaded shafts, and gears.

13. The spinal unloading apparatus according to claim 1, wherein each of the plurality of lifter assembles comprises at least one electric motor configured in combination with the worm gear and the threaded extension shaft assembly to selectively control the distance between the orthotic belts.

14. The spinal unloading apparatus according to claim 13, further comprising a portable battery pack operational to deliver power to the electric motor.

15. The spinal unloading apparatus according to claim 13, wherein the mechanical extension shaft assembly comprises at least one element selected from the group consisting of belts, pulleys, cables, threaded shafts, and gears.

16. The spinal unloading apparatus according to claim 1, further comprising a lumbar support apparatus selectively positioned between the upper and lower belts.

17. The spinal unloading apparatus according to claim 16, wherein the lumbar support comprises at least one element selected from the group consisting of support cushions, hot packs, cold packs, and electrical stimulation electrodes.

18. The spinal unloading apparatus according to claim 1, wherein at least one orthotic belt comprises integrated electrodes selectively positioned to provide a desired level of muscle or nerve stimulation in response to a desired electrical bias.

19. The spinal unloading apparatus according to claim 1, wherein at least one orthotic belt comprises at least one integrated fluidic chamber configured to substantially reduce restrictive binding associated with a user's thoracic region.

20. The spinal unloading apparatus according to claim 1, wherein at least one orthotic belt comprises at least one pocket configured to receivably accept at least one device selected from the group consisting of a cushion element, a cold element a hot element, and an electrical stimulation element.

21. The spinal unloading apparatus according to claim 1, wherein the upper orthotic belt comprises a set of selectively adjustable shoulder straps.

22. The spinal unloading apparatus according to claim 1, further comprising a recording apparatus operational to selectively record desired information associated with at least one parameter selected from the list consisting of traction, spinal unloading, stimulation, and/or therapeutic parameters.

23. A method of spinal unloading comprising:
providing an ambulatory spinal unloading apparatus that comprises a first orthotic belt, a second orthotic belt, and a plurality of lifter assemblies configured to selectively vary a distance between the orthotic belts, with each of the plurality of the lifter assemblies each comprising worm gear turning a threaded rod or a piston actuated fluidic lifting device and a residual cushioning device wherein the residual cushioning device comprises a spring and/or damper, that provides a desired residual cushioning effect achieved by compression of a spring and/or damper to thereby absorb an intermittent and/or unexpected shock and/or vibration for the treaded rod or for the piston actuated fluidic lifting device in a deactivated state.

24. The method according to claim 23, further comprising adjusting the distance between the orthotic belts by activating at least one stepper motor to control extension of a shaft assembly, such that the desired residual cushioning effect is achieved when the shaft assembly is in its fully retracted position.

25. The method according to claim 23, further comprising adjusting the distance by activating at least one electric motor to control the worm-gear and the threaded rod, such tat the desired residual cushioning effect is achieved when the threaded rod is in its frilly retracted position.

26. The method according to claim 23, further comprising the step of recording in real time, desired information associated with at least one parameter selected from the list consisting of traction, spinal unloading, stimulation, and/or therapeutic parameters.

27. The method according to claim 23, wherein the residual cushioning device comprises the spring that further cooperates with mechanical cams, and further comprising adjusting the mechanical cams against the spring to apply a desired amount of bias to achieve the desired residual cushioning effect.

28. The method according to claim 23, wherein the residual cushioning device comprises a gel-filled chamber.

29. The method according to claim 23, wherein the residual cushioning device comprises the spring.

* * * * *